United States Patent [19]
Cami et al.

[11] Patent Number: 5,376,537
[45] Date of Patent: Dec. 27, 1994

[54] PROCESS FOR PRODUCTION OF CYCLODEXTRINS

[75] Inventors: Pierre H. Cami, Nesle; Didier B. Majou, Neuilly sur Seine, both of France

[73] Assignees: Orsan, Paris, France; Mercian Corporation, Tokyo, Japan

[21] Appl. No.: 776,788

[22] Filed: Oct. 18, 1991

[30] Foreign Application Priority Data

Oct. 18, 1990 [FR] France .................................. 90 13145

[51] Int. Cl.$^5$ ............................................. C12P 19/18
[52] U.S. Cl. ...................................... 435/101; 435/95; 435/97
[58] Field of Search ...................... 435/101, 97, 95, 101

[56] References Cited

U.S. PATENT DOCUMENTS 4,477,568 10/1984 Hokse et al. ......................... 435/97

FOREIGN PATENT DOCUMENTS 2053624 4/1992 Canada .
2-249494 10/1990 Japan .
WO89/01044 2/1989 WIPO .

OTHER PUBLICATIONS

Sato et al., "Determination of CGTase from *Bacillus ohbensis*, etc.", Agric. Biol. Chem. 49(4), 1189–1191, 1985.

Horikoshi et al., "Alkalophilic Microorganisms, etc.", Research and Dev. in Japan awarded the Okochi Mem. Priz, 1982, pp. 47–52.

*Primary Examiner*—Ronald W. Griffin
*Attorney, Agent, or Firm*—Millen, White, Zelano & Branigan

[57] ABSTRACT

A process for the production of cyclodextrins, comprising reacting non-treated starch with cyclodextrin-glycosyl-transferase produced by *Bacillus ohbensis* (FERM BP-3180), or produced by a mutant derived from *Bacillus ohbensis* (e.g., FERM BP-3180), or produced by any other strain in which the CGTase gene from *B. ohbensis* has been cloned, in an aqueous solution at pH between 6.5 and 8.8 and extracting the cyclodextrins from the reaction mixture by ultrafiltration, is provided.

15 Claims, No Drawings

PROCESS FOR PRODUCTION OF CYCLODEXTRINS

BACKGROUND OF THE INVENTION

The present invention relates to a process for the production of cyclodextrins.

In particular, the invention relates to a process for the production of cyclodextrins by reaction of starch with cyclodextrin-glycosyl-transferase (CGTase) which is produced by *Bacillus ohbensis*, deposited with the Fermentation Research Institute in Japan (FRI), 1-3 Higashi-1-Chome, Tsukuba-Shi, Japan, under the Budapest Treaty, previously designated under deposit number FERM P-1990, and since 1981 designated FERM BP-3180, or produced by a mutant derived from *Bacillus ohbensis* (e.g., FERM BP-3180), or produced by any other strain in which the CGTase gene from *B. ohbensis* has been cloned. This enzyme reacts with and degrades starch to form cyclodextrins. The thusformed cyclodextrins (designated hereinbelow by CD), e.g., β-cyclodextrin (β-CD) and γ-cyclodextrin (γ-CD) are then isolated.

β-CD is a cyclic molecule consisting of 7 glucopyranose units linked to each other by 1→4 bonds; γ-CD is a cyclic molecule consisting of 8 glucopyranose units linked to each other by 1→4 bonds. These molecules possess a central hydrophobic cavity which enables the production of inclusion compounds with host molecules. The binding of the inclusion compounds occurs with low energy; thus, the inclusion phenomenon is reversible. The CDs have a particularly interesting field of application, e.g., for the encapsulation of aromas, vitamins, colors, fatty acids, pharmaceutical active principles, pesticides and fungicides. The production of β-CD and γ-CD using the CGTase produced is known.

A new α-amylase, i.e., the CGTase produced by *Bacillus ohbensis*, was first described in Japanese Patent 902415 (Japanese Application No. 7335774). Moreover, this patent discloses the preparation of β-CD and α-CD (a cyclic molecule consisting of 6 glucopyranose units linked to each other by 1→4 bonds) by reaction of liquefied or hydrolyzed starch with the CGTase produced by *Bacillus ohbensis*.

The article entitled "Determination of CGTase from *Bacillus ohbensis* and its optimum pH using HPLC", Sato, M., et al., Agricultural and Biological Chemistry, 49 (4), 1189-1991 (1985) discloses that the optimum pH of the CGTase produced by *Bacillus ohbensis* is pH 5.5. This article also specifies that the analysis by high pressure liquid chromatography (HPLC) permits a direct measurement of the cyclodextrin formed and that this method of analysis is also the most reliable.

The article entitled "Comparative studies of CGTases from *Bacillus ohbensis*, *Bacillus macetans* and *Bacillus circulans* and production of cyclodextrins using those CGTases", Yagi, Y., et al., J. Jpn. Soc. Starch Sci., 33, 144-151 (1986), discloses the following information:
- the optimum pH for the CGTase produced by *Bacillus ohbensis* is pH 5.5;
- the CGTase produced by *Bacillus ohbensis* put into reaction with liquid starch produces β-CD and γ-CD;
- with liquefied starch and CGTase produced by *Bacillus ohbensis*, a yield of 21.6% by weight of CD is obtained at pH values between 5 and 10.

EP-A-220719 describes a process for the production of cyclodextrins (α, β and γ) according to which liquefied starch is subjected to CGTase produced by *Bacillus ohbensis* with a pH preferably maintained between 6.5 and 7.5.

The cyclodextrins formed by this reaction are typically extracted from the reaction mixture by adsorption on a water insoluble resin, the ligand of which has such a size to be included in the cyclodextrins, and in that way, forms inclusion compounds.

This process favors the formation of cyclodextrins as well as the purification of these pro-ducts which are then eluted with warm water or with a mixture of water and alcohol: however, this extraction process is expensive and complicated, and the concentration of the cyclodextrins of these aqueous solutions is very low; it does not exceed 8 g/l.

SUMMARY OF THE INVENTION

The present invention provides an improved process for the production of β-CD and γ-CD which provides far better yields and is simpler than the prior process, as well as improving yields of β-CD and not requiring treated starch as a new material.

Surprisingly, this object is accomplished by a process for the production of cyclodextrins comprising reacting non-treated starch with cyclodextrin-glycosyl-transferase produced by *Bacillus ohbensis*, (FERM BP-3180), or produced by a mutant derived from *Bacillus ohbensis* (e.g., FERM BP-3180), or produced by any other strain in which the CGTase gene from *B. ohbensis* has been cloned, in an aqueous solution at pH between 6.5 and 8.8 and extracting the cyclodextrins from the reaction mixture by ultrafiltration.

Upon further study of the specification and appended claims, further objects and advantages of this invention will become apparent to those skilled in the art.

By "B.O. enzyme" as used herein is meant the cyclodextrin-glycosyl-transferase produced by *Bacillus ohbensis*, (FERM BP-3180), or produced by a mutant derived from *Bacillus ohbensis* (e.g., FERM BP-3180), or produced by any other strain in which the CGTase gene from *B. ohbensis* has been cloned.

Other strains other than *Bacillus ohbensis* in which a CGTase gene from *Bacillus ohbensis* has been cloned include, e.g., the *Escherichia coli* described in Sin, K-A., et al., Appl. Microbiol. Biotechnol. 33, 600-605 (1991).

In a preferred aspect, the process according to the invention is operated continuously.

This process has the advantage, inter alia, of enabling production of a high yield of β-CD, approaching 40% or more, relative to the quantity of starch supplied.

Another advantage of the invention is that the reaction can utilize raw starch, i.e., starch which has not been by subjected to chemical or thermal treatment, or to treatment with a starch thinning enzyme such as, e.g., amylase. Indeed, contrary to the well-known processes, in the process according to the invention, the starch does not require any treatment (e.g., gelatinization, liquefaction or dextrinization) before being subjected to enzymatic conversion to CDs as herein disclosed. The raw starch can be in the form of powder or of a starch milk, i.e., an aqueous suspension.

When the starch is in powder form, it is preferable to utilize a grain size not exceeding 200μ. Otherwise, a system of protection for the ultrafiltration system in order to avoid its obstruction must be provided.

Any kind of starch can be utilized. For example, suitable sources of starch include starch from potato, maize, wheat and manioc. It is preferable to use potato flour. It is also preferred that the concentration of starch in the reaction mixture does not exceed 15% by weight, and more preferably, 8–10% by weight.

According to the process of the invention, the pH of the reaction mixture is most preferably maintained between pH 6.5 and 8.8. Outside of this pH range, considerable reduction of the ultrafiltration flow develops from the obstruction of the ultrafiltration membrane, which further results in decreases in yield.

The pH value is adjusted to the preferred range according to the origin of the non-treated starch. The best yields and efficiency of production of β-CD have been obtained with non-treated wheat starch reacted at a pH between 7 and 7.5. For non-treated potato starch, the reaction is preferably conducted at a pH between about 7.5 and 8.8. The best yields and efficiency of production of β-CD from non-treated potato starch have been reached by conducting the reaction at a pH between 8 and 8.5.

To avoid a premature deactivation of the B.O. enzyme, the reaction temperature preferably should not exceed 65° C. and more preferably should be maintained between 55 and 60° C.

It is also preferable to stabilize the activity of the B.O. enzyme, e.g., by means of calcium salts such as calcium chloride. The supply of calcium in the reaction mixture can be provided by using non-demineralized water or by adding calcium salts, such that a final concentration of about 0.01% by weight is achieved.

To provide good enzymatic activity and consequently to ensure good yields and efficiency of production of CD, the concentration of B.O. enzyme is preferably between 1–10 U/g of starch, as determined by HPLC chromatography according to the method described in Agricultural and Biological Chemistry (1985) supra. A unit of B.O. enzyme is defined as the quantity of enzyme producing 1 μmole of CD per min. at 50° C.

The B.O. enzyme is more specific for the production of β-CD. However, starch subjected to this enzyme also yields γ-CD. The process according to this invention may therefore be used for the production of γ-CD. On the other hand, the production of α-CD from starch treated with B.O. enzyme is virtually non-existent.

In the course of their formation according to the present invention, the β-CD and γ-CD are extracted from the reaction mixture by means of ultrafiltration, while the enzyme, starch and starch dextrinized by the B.O. enzyme are retained in the reaction mixture.

The quantity of water in the reaction mixture can be kept almost constant in the reactor and the concentration of starch can be maintained by successive or continuous addition.

The ultrafiltration is generally accomplished by a conventional ultrafiltration device which is associated with the reactor where the enzymatic conversion takes place. The ultrafiltration device essentially includes a membrane, preferably a tubular one, with a molecular weight cutoff higher to the molecular weight of the γ-CD and lower to the molecular weight of the B.O. enzyme. Thus, for example, a membrane having a molecular weight cutoff of between 2000 and 30,000 Daltons is suitable. A suitable ultrafiltration membrane may be, e.g., organic or mineral, and may be planar or made with hollow fibers. Suitable mineral membranes for use in the present invention include, e.g., membranes made of a carbon support material and a filter of zircon, or a ceramic membrane. Suitable organic membranes for use in the present invention include, e.g., membranes made of polysulfone, polyacrylonitrile, fluorinated or cellulosic polymers. Specific examples include the plane membranes manufactured under the commercial name DDS ™ (deanske Sukkerfabrikker, Nakskov, Denmark) having a molecular weight cutoff over 2000 Daltons, or the hollow fiber membranes made under the commercial name ROMICON ™ (Romincon Inc., Woburn, Mass.).

The optimum productivity of the system composed of the reactor and the ultrafiltration device is obtained with high ultrafiltration flows and concentrations in β-CD in the permeate maintained at between 10 g/l and 20 g/l. The ultrafiltration membrane is preferably subjected to transmembrane pressures between 1–2 bar. The volume of the reaction mixture in the reactor is preferably maintained such that the reactor has a capacity of 1–5 times the volume of the reaction mixture, and thus, according to the operating conditions, allows the maintenance of optimum residence time. It is also preferable to have a system for ultrafiltration with a turnover of the reaction volume of ½ to 2 hours, the overage concentration of β-CD in the permeate being maintained at between 8 g/l and 15 g/l. Under these conditions, the process according to the invention enables production of more than 0.5 kg of β-CD per hour per $m^2$ of membrane, and this productivity can reach 1 $kg/h/m^2$ in some cases.

According to a second aspect of this invention, the process of the invention is performed continuously, as follows:
- the temperature, pH and concentration of starch, agitated in water with the B.O. enzyme is adjusted to the desired values, thus ensuring optimum control of the process parameters and avoiding, due to regulation of starch input, the formation of a gel or aggregate in the reactor;
- when the desired viscosity is reached, the ultrafiltration device is set in operation and the concentration of the reactants in the reactor adjusted by adding water, and the thus-produced cyclodextrins are continuously extracted in the permeate; it is not necessary to add more starch, resulting in a gradual decrease in the reaction volume in the reactor.

The permeate collected in an aqueous solution containing primarily β-CD as well as γ-CD and dextrins of low molecular weight. After partial elimination of water from the permeate, an aqueous solution is obtained which is concentrated in β-CD, γ-CD and dextrins; this solution may be used "as is" to prepare inclusion compounds.

Alternatively, and preferably, the β-CD can be extracted from the permeate. The collection of the β-CD from the permeate can be performed by concentration of the permeate followed by a crystallization. The concentration of the permeate can be performed by evaporation under low pressure or by reverse osmosis. The crystallization is performed by evaporation followed by cooling. After separation of the crystals of β-CD, the γ-CD can be extracted from the mother liquor of crystallization.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, and of corresponding application France 90/13145, are hereby incorporated by reference.

EXAMPLES

Example 1

In a reactor, while stirring, 3680 g of potato flour, corresponding to a concentration of 8% by weight of starch, is progressively added into suspension in water. The temperature is regulated to 58° C.±2° C. and the pH is adjusted to 8.2±0.2, and the B.O. enzyme is introduced in a quantity of 2.5 U/g of starch.

As soon as the production of cyclodextrins begins in the reaction mixture, the ultrafiltration system is fed from the reactor. The ultrafiltration membrane used is a mineral membrane with a support of carbon and a filter of zircon. It has a molecular weight cutoff of 15,000 Daltons and a water flow of 800 l/h/m² under 4 bar at 25° C. The pressure is regulated in order to obtain an average ultrafiltration flow of 65 l/h/m². The flow of ultrafiltration remains stable over time.

The retentate of ultrafiltration is recycled into the reactor and the cyclodextrins are recovered from the permeate.

In the reactor, the level of solution which forms the reaction mixture is maintained by addition of water, and the concentration of starch maintained by addition of starch.

The permeate is concentrated by evaporation, and the cyclodextrins crystallized in a crystallizer. 1100 g of $\beta$-CD is obtained as white crystals. The yield of $\beta$-CD production relative to starch used in 29.9% after 7 hours of reaction.

Example 2

The operating mode followed in this example is the same as in Example 1, except for the following:
262 kg non-treated potato starch used (i.e., 10% by weight in the reaction mixture);
3 U/g B.O. enzyme;
average ultrafiltration flow rate is 56.4 l/h/m² of the membrane.
The results obtained are as follows:
104 kg $\beta$-CD after 40 hours of reaction;
yield of $\beta$-CD is 39.7% relative to the quantity of starch used.

Simultaneously with the production of $\beta$-CD, there is production of $\gamma$-CD. The solubility of $\beta$-CD in water being different from that of $\gamma$-CD, the $\beta$-CD can be separated from $\gamma$-CD by concentration and crystallization of the permeate:
yield of $\gamma$-CD in the mother liquor of crystallization is 25 kg;
this yield of $\gamma$-CD relative to the quantity of starch used is 9.5%.

Example 3

The operating mode followed in this example is the same as in Example 1, with the following differences:
dry weight of non-treated potato starch used is 1322 g;
3 U/g B.O. enzyme;
pH 8.6;
temperature 58° C.;
average ultrafiltration flow rate is 15 l/h/m² of membrane;
membrane used is a DDS organic membrane with a molecular weight cutoff of 6000 Daltons.
The results obtained are as follows:
476 kg $\beta$-CD;
yield of $\beta$-CD is 36% relative to the quantity of starch used after 6.5 hours of reaction.

Example 5

The operating mode followed in this example is the same as in Example 1, with the following differences:
dry weight of non-treated potato starch used is 3555 g;
3 U/g B.O. enzyme;
pH 8.6;
temperature 58° C.;
average ultrafiltration flow rate is 26 l/h/m² of membrane;
membrane used is a ceramic membrane commercialized under the name SCT with an average diameter of the pores of 200 Å.
The results obtained are as follows:
824 kg $\beta$-CD after 5 hours of reaction;
yield of $\beta$-CD is 42% relative to the quantity of consumed starch after 5 hours of reaction.

Example 6

The operating mode followed in this example is the same as in Example 1, with the following differences:
weight of non-treated potato starch used is 435 g (i.e., 10% by weight in the reaction mixture);
3 U/g B.O. enzyme;
pH 7.2;
average ultrafiltration flow rate is 59 l/h/m² of membrane;
The results obtained are as follows:
35 kg $\beta$-CD after 38 hours of reaction;
yield of $\beta$-CD is 8% relative to the quantity of starch used.

Example 7

A stirring reactor combined with an ultrafiltration device called 2S7 TM (Techsep, St. Maurice de Beynost, France) is used, equipped with mineral membranes with a carbon support and a zircon filter, having a molecular weight cutoff of 15,000 Daltons. 1800 g of non-treated wheat starch of dry extract 85%, in a total volume of 20 liters of water are used. The temperature of the reaction mixture is adjusted to 60° C. Four tests were performed using 4630 U of B.O. enzyme as follows:

| Tests | a) | b) | c) | d) |
| --- | --- | --- | --- | --- |
| ultrafiltration flow (l/h) | 30 | 20 | 20 | 20 |
| pH adjusted to | 8.2 | 8 | 7.5 | 7.5 |
| addition of starch | 5 × 500 | 5 × 300 | 4 × 300 | 4 × 250 |
| test duration (h) | 8 | 7 | 7.5 | 7.5 |

The additions of starch were performed each hour, the first one 1 hour after the start of production. The permeate is collected continuously, the liquid level in the reactor remaining constant by addition of water.

| Results obtained | a) | b) | c) | d) |
|---|---|---|---|---|
| β-CD produced (g) | 1011 | 986 | 882 | 780 |
| γ-CD produced (g) | 221 | 218 | 253 | 217 |
| β-CD/consumed starch | 31 | 36 | 41 | 38.4 |

The productivity and yield of the reaction performed with wheat starch are about the same as achieved with potato starch.

Example 8

The same apparatus is used as in Example 7, with the following differences:
1800 g of maize starch used per 20 l of water;
temperature is 60° C.;
pH adjusted to 8;
3850 U of B.O. enzyme.

The permeate flow was adjusted to 20 l/h. During 15 hours, 5000 g of maize starch is added.

In 15 hours, 610 g of β-CD and 180 g of γ-CD is produced. The yield in β-CD relative to the quantity of dry starch used is 18%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of β-cyclodextrin and γ-cyclodextrin, comprising
reacting raw, non-treated starch in an aqueous solution at pH between 6.5 and 8.8 with cyclodextrin-glycosyl-transferase produced by *Bacillus ohbensis*, (FERM BP-3180), produced by a mutant derived from *Bacillus ohbensis*, or produced by another strain in which the CGTase gene from *B. ohbensis* has been cloned, whereby said CGTase produces, under said conditions, substantially no α-cyclodextrin, and
extracting the thus-produced cyclodextrins from the reaction mixture by ultrafiltration.

2. A process of claim 1, wherein the starch is potato, maize, wheat or manioc starch.

3. A process of claim 1, wherein the concentration of starch is 15% by weight or less.

4. A process of claim 3, wherein the concentration of starch is included between 8 and 10% by weight.

5. A process of claim 2, wherein the starch is non-treated wheat starch and the reaction is conducted at a pH included between 7 and 7.5.

6. A process of claim 2, wherein the starch is non-treated potato starch and the reaction is conducted at a pH included between 7.5 and 8.8.

7. A process of claim 6, wherein the reaction is conducted at a pH included between 8 and 8.5.

8. A process of claim 1, wherein the reaction is conducted at a temperature of 65° C. or less.

9. A process of claim 8, wherein the reaction is conducted at a temperature included between 55° C. and 60° C.

10. A process of claim 1, wherein the reaction is conducted at a concentration of cyclodextrin-glycosyl-transferase included between 1 and 10 U/g of starch used.

11. A process of claim 1, wherein the reaction is conducted in a reaction system comprising
a reactor; and
an ultrafiltration device; wherein the average residence time of the starch used in the system is adjusted, the turnover time for the reaction volume is between ½ and 2 hours, and the average concentration of β-cyclodextrin in the permeate is included between 8 g/l and 15 g/l.

12. A process of claim 1, further comprising preferentially crystallizing out the thus-produced β-CD from the ultrafiltration permeate.

13. A process of claim 12, wherein the yield of β-CD per gram of starch consumed is at least 40%.

14. A process of claim 12, further comprising recovering the thus-produced γ-CD from the mother liquor of crystallization.

15. A process of claim 14, wherein the yield of γ-CD per gram of starch consumed is at least 9%.

* * * * *